United States Patent [19]

Hughson et al.

[11] Patent Number: 4,582,196
[45] Date of Patent: Apr. 15, 1986

[54] YARN DISPENSER

[76] Inventors: Sharon J. Hughson; Jerry R. Hughson, Sr., both of 6677 Iris Ave., Cincinnati, Ohio 45213

[21] Appl. No.: 672,816

[22] Filed: Nov. 19, 1984

[51] Int. Cl.⁴ ................... A61B 17/06; B65D 85/04
[52] U.S. Cl. .................. 206/63.3; 206/83; 206/49; 206/392; 206/394; 206/416
[58] Field of Search .......... 206/63.3, 49, 392, 83, 206/394, 416

[56] References Cited

U.S. PATENT DOCUMENTS

| 1,103,227 | 7/1914 | Stratton | 206/63.3 |
| 1,718,078 | 6/1929 | Ritchie | 206/63.3 |
| 3,648,949 | 3/1972 | Berger et al. | 206/63.3 |
| 4,084,692 | 4/1978 | Bilweis | 206/63.3 |

FOREIGN PATENT DOCUMENTS

| 705747 | 3/1965 | Canada | 206/63.3 |
| 1195425 | 4/1958 | France | 206/63.3 |
| 624072 | 8/1961 | Italy | 206/63.3 |

*Primary Examiner*—Joseph Man-Fu Moy
*Attorney, Agent, or Firm*—Wood, Herron & Evans

[57] ABSTRACT

The purpose of the yarn dispenser is to store and dispense embroidery floss in a orderly manner.

The operation of the device involves placing a skein of floss over the two bushings which rotate on internal axles. After the two halves of the outer case are assembled, the outside end of the skein is drawn out through the dispensing hole and cut off as needed by the user.

An abraded area is provided to record information about the skein inside, and windows (holes) are provided to permit the user to see the color and amount of floss remaining.

10 Claims, 2 Drawing Figures

YARN DISPENSER

SUMMARY

The purpose of the invention is to temporarily store and to dispense embroidery floss, a fine yarn used in needlework (candlewicking, cross stitching, etc.) projects. Floss is sold by the skein, a single loop of approximately 11.5 inches in circumference and is bound in the middle by paper bands containing dye lot information.

Once the bands are removed they are prone to loss, and the skein tends to unravel and to tangle with use and storage. All existing storage devices either fail to allow for orderly dispensing, require rewinding on a spindle or require precutting of the floss into uniform lengths.

The use of the yarn dispenser described herein eliminates the above problems by storing a complete skein in a secure holder and allowing the user to withdraw only the amount needed at the time.

DETAILED DESCRIPTION

Figure 1:
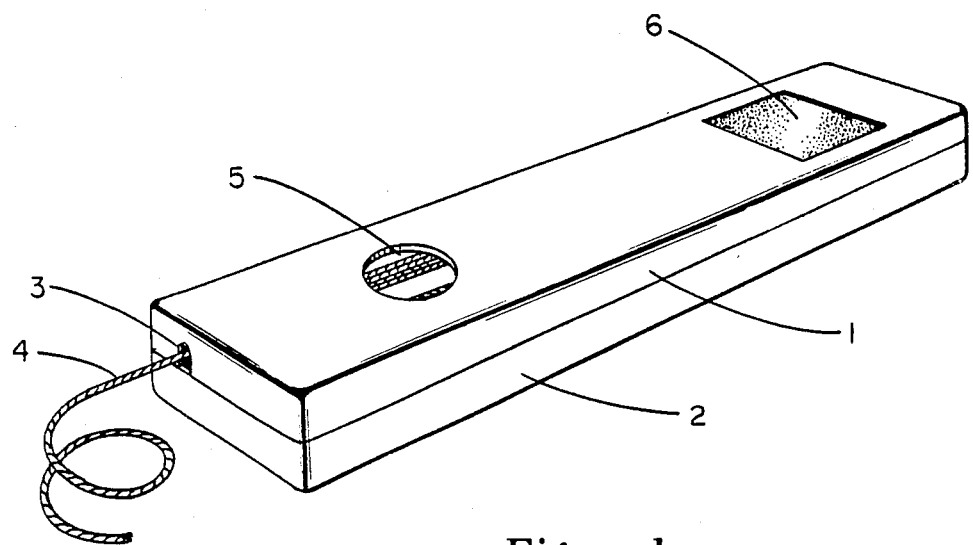
FIG. 1 shows the assembled yarn dispenser in perspective.

The yarn dispenser, as depicted in FIG. 1 is an opaque plastic container consisting of two identical halves (1&2) which snap together. A hole (3) in each end allows embroidery floss (4) to be pulled from a skein held within. Circular windows (5) allow the user to see the color and amount of floss inside. When assembled the outside dimensions are as follows: lengt=6.5 inches; width=0.0875 inch and height=0.625 inch. The walls of the yarn dispenser are 0.0625 inch thick.

The interior and exterior finish is smooth except for an abraded area (6) which allows the user to record the floss dye lot number with a pencil or other erasable marker.

Figure 2:
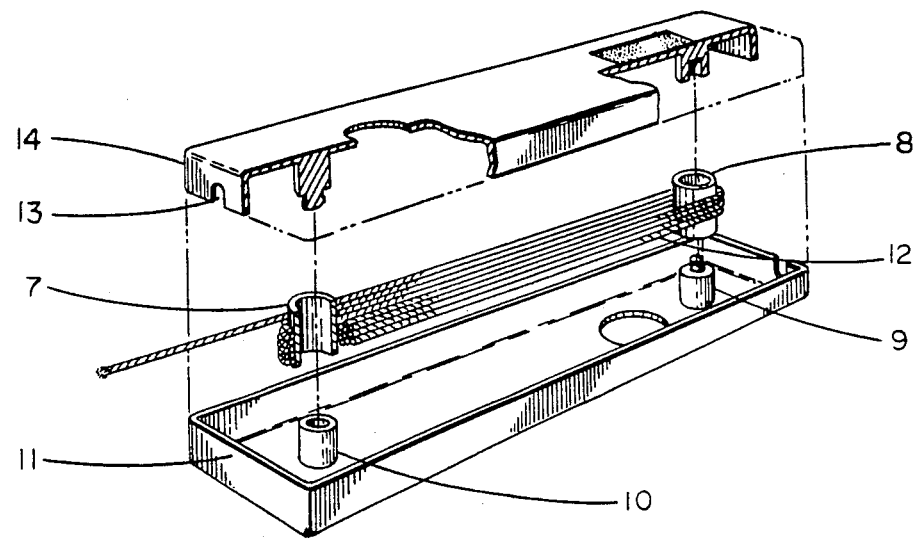
FIG. 2 is an exploded perspective drawing illustrating the construction, features and application of the invention.

FIG. 2 depicts the internal construction, assembly and operation of the yarn dispenser.

To assemble and use the device, two bushings (7&8) are placed over the bottom halves to the axles (9&10) molded to the outer shell (11) and located 0.625 inch from each end. The bushings have an inside diameter of 0.25 inch, and an outside diameter of 0.375 inch. Their height is 0.46875 inch. The axles have an outside diameter of 0.1875 inch. A skein of floss (12) is then placed over the bushings, with the outside strand of the skein extending beyond an end wall, in line with the off-set dispensing hole (13). The top half (14) is then placed down over the bottom half (11) allowing the axle halves to snap together forming a friction bond sufficiently tight to hold the two halves together and loose enough to allow the user to disassemble the unit when desired.

Once assembled in the above manner, the skein of floss fits snugly over the bushings (7&8), which fit loosely on the axles (9&10), allowing free rotation of the skein as the exposed strand is drawn out through the end hole by the user.

What is claimed is:

1. A dispenser for yarn such as embroidery floss comprising:

an elongated container having a first end and a second end and defining an interior area, the container including, in the interior area, a first axle near the first end of the container and a second axle near the second end of the container; and a bushing rotatably received on the second axle, the container including a yarn opening near the first end of the container, whereby an elongated skein of yarn, positioned to surround the first axle and the bushing on the second axle and having a free end extending from the interior area of the container through the yarn opening to the outside of the container, may be withdrawn from the container by pulling on the free end of the yarn.

2. The dispenser of claim 1 comprising a first bushing rotatably received on the first axle of the container and a second bushing rotatably received on the second axle of the container.

3. The dispenser of claim 2 in which the container further includes a yarn opening near the second end of the container, whereby a free end of a skein of yarn may extend from the interior area of the container through either the yarn opening near the first end of the container or the yarn opening near the second end of the container.

4. The dispenser of claim 1 in which the elongated container comprises two elongated container elements interfit with one another to form the elongated container.

5. The dispenser of claim 4 in which each container element has a first end and a second end and each includes a first axle portion near its first end and a second axle portion near its second end.

6. The dispenser of claim 5 in which the first container element is substantially identical to the second container element, and the two container elements are interfit with one another to form the elongated container, with the first end of the first container element being adjacent the second end of the second container element and the second end of the first container element being adjacent the first end of the second container element.

7. The dispenser of claim 6 in which each container element includes an opening therein permitting viewing of yarn in the interior area of the container.

8. A dispenser for yarn such as embroidery floss comprising:

a container defining an interior area and including, in the interior area, a first axle and a second axle;

a first bushing rotatably received on the first axle; and a second bushing rotatably received on the second axle, the container including a yarn opening, whereby a skein of yarn, positioned to surround the first bushing and the second bushing and having a free end extending from the interior area of the container through the yarn opening to the outside of the container, may be withdrawn from the container by pulling on the free end of the yarn.

9. The dispenser of claim 8 in which the container comprises a pair of interfitting container elements.

10. The dispenser of claim 8 in which the container has a first end and a second end and the centers of the first and second ends of the container are substantially aligned with the first and second axles of the container, the first end of the container defining said yarn opening at a location offset from the center of the first end of the container.

* * * * *